United States Patent
Fujisawa et al.

(10) Patent No.: US 7,028,773 B2
(45) Date of Patent: Apr. 18, 2006

(54) ASSESSING DOWNHOLE WBM-CONTAMINATED CONNATE WATER

(75) Inventors: Go Fujisawa, Danbury, CT (US);
Oliver C. Mullins, Ridgefield, CT (US); Chengli Dong, Sugar Land, TX (US); Andrew Kurkjian, Sugar Land, TX (US)

(73) Assignee: Schlumberger Technology Coporation, Ridgefield, CT (US)

( * ) Notice: Subject to any disclaimer, the term of this patent is extended or adjusted under 35 U.S.C. 154(b) by 464 days.

(21) Appl. No.: 10/318,800

(22) Filed: Dec. 13, 2002

(65) Prior Publication Data

US 2004/0000400 A1 Jan. 1, 2004

Related U.S. Application Data

(63) Continuation-in-part of application No. 10/305,878, filed on Nov. 27, 2002, now Pat. No. 6,729,400.
(60) Provisional application No. 60/391,570, filed on Jun. 26, 2002, and provisional application No. 60/333,890, filed on Nov. 28, 2001.

(51) Int. Cl.
*E21B 43/00* (2006.01)
*G01V 8/00* (2006.01)

(52) U.S. Cl. .................. 166/250.12; 166/264; 250/255; 250/259
(58) Field of Classification Search ............ 166/250.01, 166/250, 250.12, 66, 264, 250.02; 250/259, 250/255
See application file for complete search history.

(56) References Cited

U.S. PATENT DOCUMENTS 3,780,575 A    12/1973 Urbanosky .............. 73/152
3,859,851 A    1/1975 Urbanosky .............. 73/155
4,716,973 A *  1/1988 Cobern .................. 175/50

(Continued)

OTHER PUBLICATIONS

Downare, T. D. et al. "Visible and Near–Infrared Fluorescence of Crude Oils". *Applied Spectroscopy*, vol. 49, No. 6, (1995), pp. 754–764.
Mullins, O. C. et al. "Downhole Determination of GOR on Single–Phase Fluids by Optical Spectroscopy". *SPWLA 42nd Annual Symposium*, Paper M, (2001), pp. 1–14.

(Continued)

*Primary Examiner*—Kenn Thompson
(74) *Attorney, Agent, or Firm*—John L. Lee; William B. Batzer; Dale Gaudier

(57) ABSTRACT

Water-based mud filtrate concentration in a downhole fluid sample drawn from the borehole of an oil well is assessed. To measure water-based mud filtrate concentration, a water-based mud having a water-soluble fluorescent dye tracer is pumped into the borehole; sample fluid from a selected downhole location is pumped through a downhole flow line having a window; sample fluid flowing in an excitation region of the downhole flow line is illuminated through the window with fluorescence excitation light; and fluorescence emission from the excitation region is measured to produce a measured value. The measured value represents the fraction of water-based mud filtrate in the sample fluid. A calibration value is determined representing 100% water-based mud filtrate. A method for validating a sample of connate water as having an acceptably low WBM filtrate contamination tests for validation downhole, in real time. Each measured value of the series of measured values is compared with a predetermined fraction of a calibration value. Samples that are validated may be captured and brought to the surface for analysis. A method using the time series data and a predetermined fraction of the calibration value calculates a predicted flushing time to completion.

11 Claims, 10 Drawing Sheets

U.S. PATENT DOCUMENTS

| | | | |
|---|---|---|---|
| 4,860,581 A | | 8/1989 | Zimmerman et al. .......... 73/155 |
| 4,994,671 A | | 2/1991 | Safinya et al. ............... 250/255 |
| 5,167,149 A | | 12/1992 | Mullins et al. ................ 73/155 |
| 5,335,542 A | * | 8/1994 | Ramakrishnan et al. . 73/152.08 |
| 5,939,717 A | | 8/1999 | Mullins ....................... 250/255 |
| 6,274,865 B1 | * | 8/2001 | Schroer et al. ........... 250/269.1 |
| 6,564,866 B1 | * | 5/2003 | Clark et al. ............. 166/250.12 |
| 6,645,769 B1 | * | 11/2003 | Tayebi et al. .................. 436/56 |
| 6,714,872 B1 | * | 3/2004 | DiFoggio et al. .............. 702/12 |
| 6,729,400 B1 | * | 5/2004 | Mullins et al. .............. 166/264 |

OTHER PUBLICATIONS

Ralston, C. Y. et al. "Quantum Yields of Crude Oils". *Applied Spectroscopy*, vol. 50, No. 12, (1996), pp. 1563–1568.

Wang, X. et al. "Fluorescence Lifetime Studies of Crude Oils". *Applied Spectroscopy*, vol. 48, No. 8, (1994), pp. 977–984.

* cited by examiner

ASSESSING DOWNHOLE WBM-CONTAMINATED CONNATE WATER

This application is a co-owned, U.S. continuation-in-part of application Ser. No. 10/305,878, filed Nov. 27, 2002, now issued as U.S. Pat. No. 6,729,400, which claims the benefit of U.S. Provisional Application No. 60/333,890, filed Nov. 28, 2001. This application also claims the benefit of U.S. Provisional Application No. 60/391,570, filed Jun. 26, 2002.

FIELD OF THE INVENTION

The invention is directed to evaluating new petroleum discoveries by analysis of fluid samples acquired by wireline fluid sampling (WFS) from an oilfield reservoir. In particular, the invention is directed to a method and apparatus for measuring downhole water-based mud (WBM) filtrate concentration in a sample of connate water before the sample is brought to the surface.

BACKGROUND OF THE INVENTION

In evaluating a new petroleum discovery, formation fluid samples are acquired for analysis. Such samples are typically acquired by open-hole wireline fluid sampling (WFS) and brought to the surface for analysis. Accordingly, as currently practiced, mud filtrate contamination of a sample is typically not measured until after the sample is brought to the surface. If excessive mud filtrate contamination is detected after the sample is brought to the surface, the sample is deemed invalid and is discarded. Even if the sample is suitable for use, time has usually been wasted in extra flushing of the sampling tool when an earlier sample would have been good enough.

There are four situations involving oil based mud (OBM) filtrate or water based mud (WBM) filtrate contamination of formation fluid samples. These are OBM filtrate contamination of oil samples; WBM filtrate contamination of oil samples; OBM filtrate contamination of connate water samples; and WBM filtrate contamination of connate water samples. The last situation, WBM filtrate contamination of connate water samples, is not addressed in the prior art. Thus, there is an unfulfilled need for a method and apparatus for measuring downhole water-based mud (WBM) filtrate concentration in a sample of connate water before the sample is brought to the surface.

SUMMARY OF THE INVENTION

The invention provides a method and apparatus for assessing water-based mud filtrate concentration in a downhole fluid sample drawn from the borehole of an oil well.

The invention provides a method for measuring water-based mud filtrate concentration. The method includes pumping a water-based mud having a water-soluble fluorescent dye tracer into the borehole; pumping sample fluid from a selected downhole location through a downhole flow line; illuminating sample fluid in an excitation region of the downhole flow line with fluorescence excitation light; and measuring fluorescence emission from the excitation region to produce a measured value representing the fraction of water-based mud filtrate in the sample fluid.

The invention provides a tool including an elongated body containing a flow line having a window, the flow line containing an excitation region proximate to the window; and a pump configured to pump sample fluid from a selected downhole location through the flow line.

The invention further provides a method for establishing a calibration value representing 100% water-based mud filtrate. In a preferred embodiment, the calibration value is established by pumping substantially 100% water-based mud filtrate through the downhole flow line and measuring fluorescence emission from the excitation region. In another embodiment, the calibration value is established by measuring fluorescence emission in a laboratory.

The invention further provides a method and apparatus for validating a sample of connate water as having an acceptably low WBM filtrate contamination. Each sample is drawn from formation at a selected depth and tested for validation downhole, in real time. Each measured value of the series of measured values is compared with a predetermined fraction of a calibration value. Samples that are validated may be captured and brought to the surface for analysis.

The invention further provides a method and apparatus for using the time series data and a predetermined fraction of the calibration value to calculate a predicted flushing time to completion.

DETAILED DESCRIPTION

Figure 1:
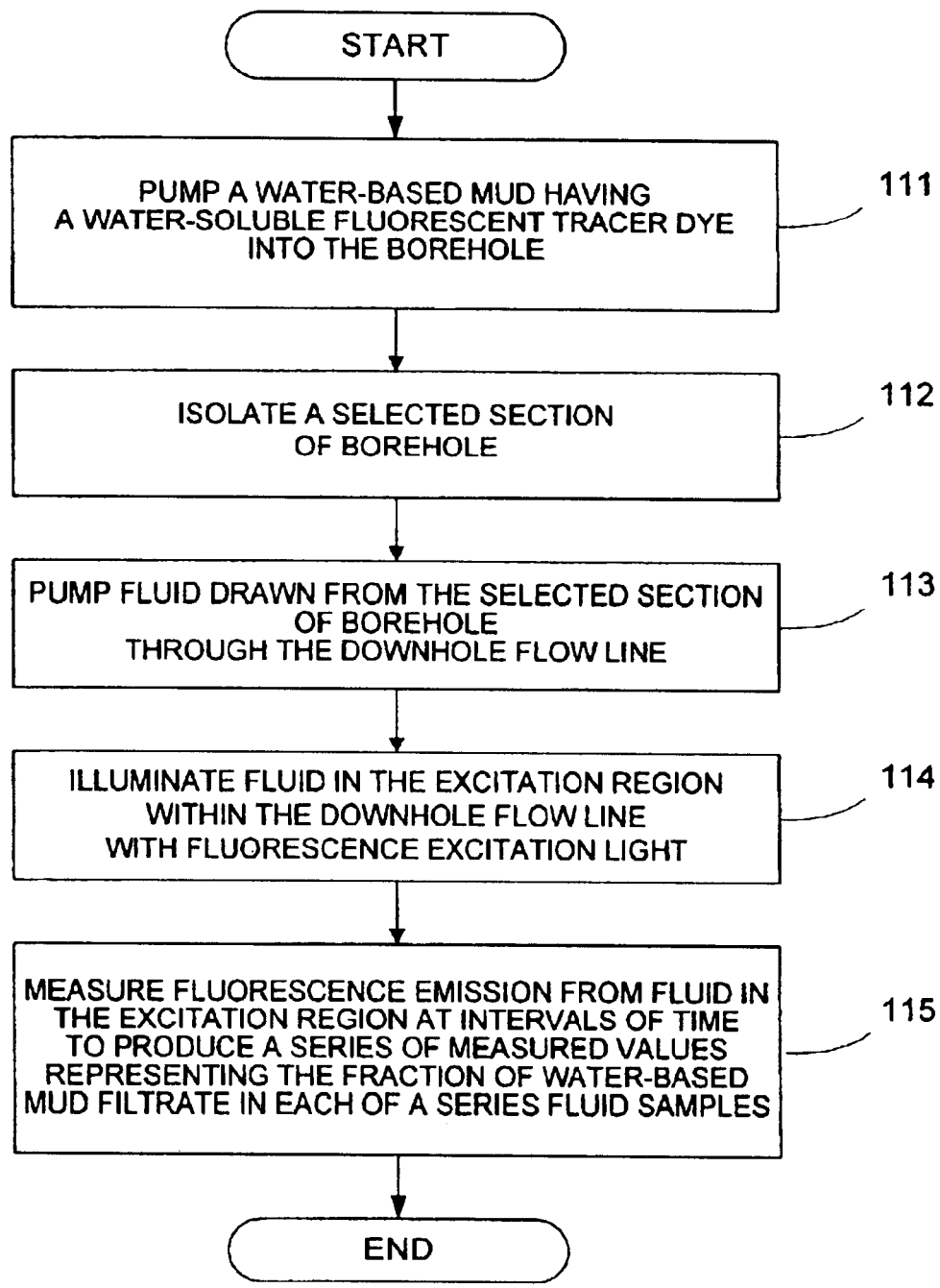
FIG. 1 is a flowchart of a first preferred embodiment of a method for measuring downhole, in real time, water-based mud (WBM) filtrate concentration in a sample of connate water drawn from formation surrounding a well.

The invention provides a method, illustrated in FIG. 1, for measuring downhole, in real time, water-based mud (WBM) filtrate concentration in a sample of connate water drawn from formation surrounding a well. The method includes stimulating fluorescence in a tracer dye in the WBM and measuring fluorescence emission.

Figure 2:
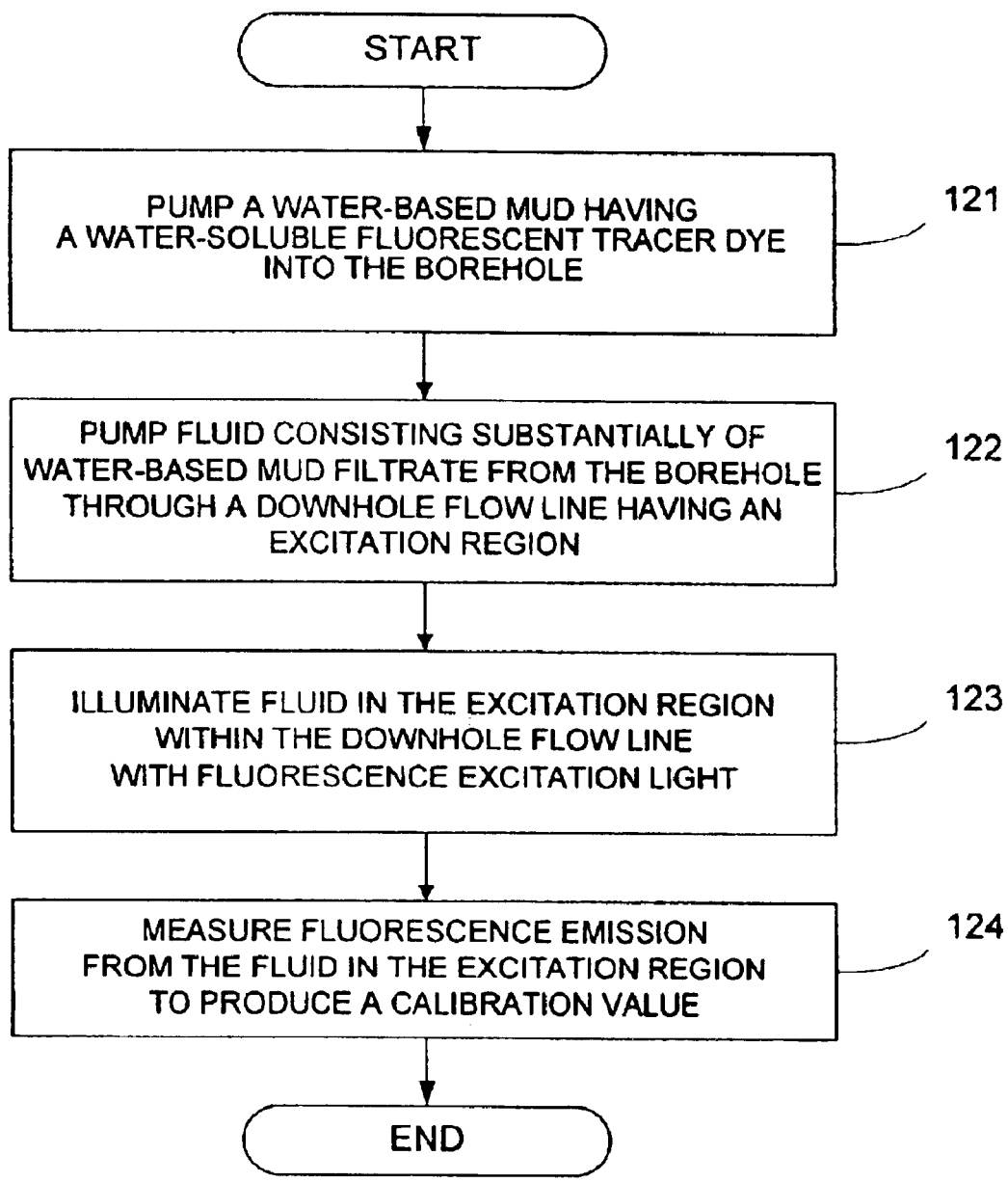
FIG. 2 is a flowchart of a first preferred embodiment of a method for calibrating the fluorescence monitor in situ.

Preferably, the fluorescence monitor is calibrated in situ by the method illustrated in FIG. 2.

Figure 10:
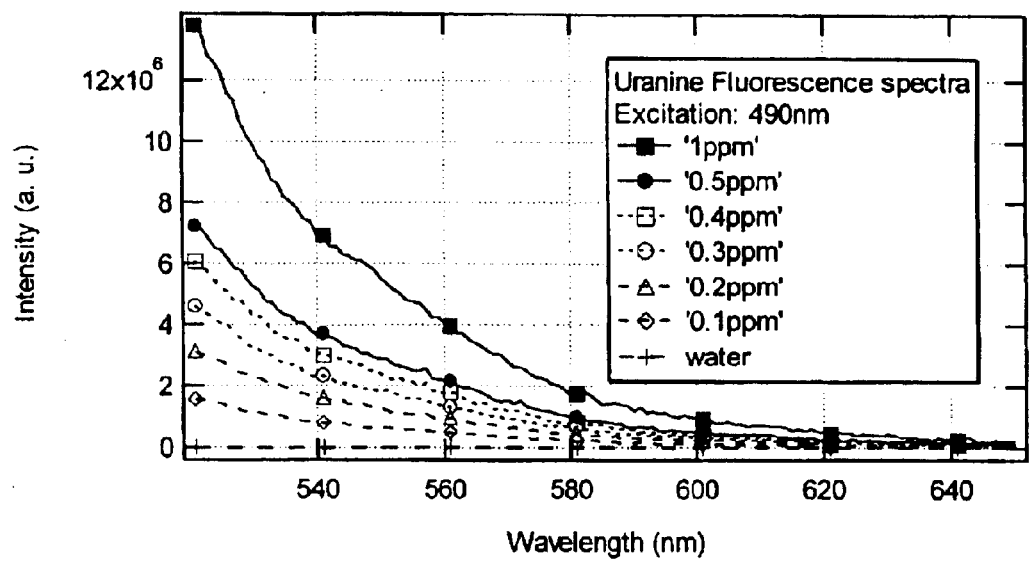
FIG. 10 is a graph showing fluorescence spectra measured using a laboratory spectrometer.
Figure 11:
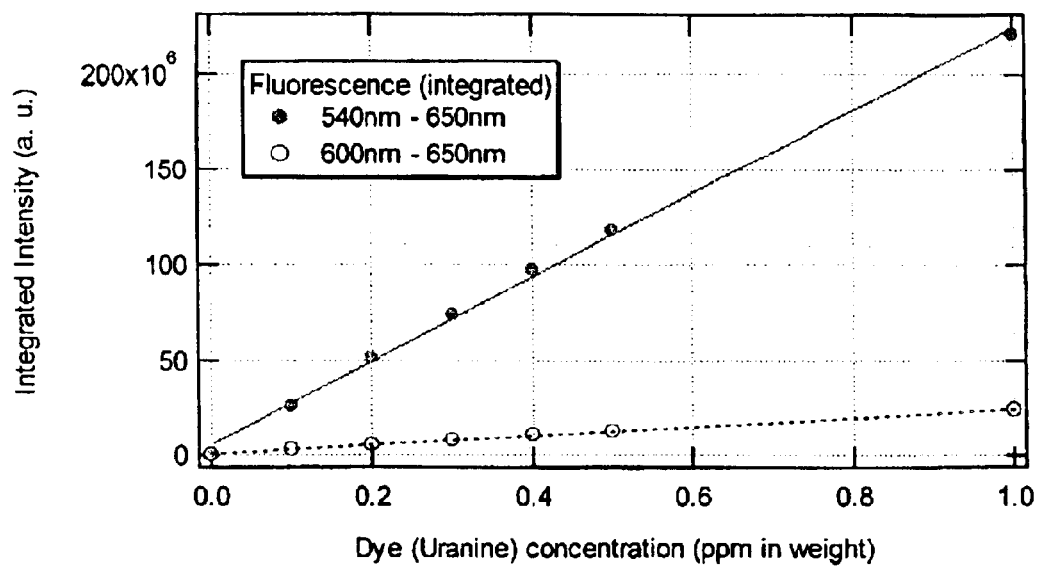
FIG. 11 is a graph showing integrated fluorescence signal for the preferred embodiment of the invention.

Alternatively, the fluorescence monitor may be calibrated in the laboratory prior to operation in a borehole based on data provided in the graphs of FIGS. 10 and 11. FIGS. 10 and 11 show an example of calibration that involves seven calibration fluids: 1 ppm (100% mud), 0.5 ppm (50% mud), 0.4 ppm (40% mud), 0.3 ppm (30% mud), 0.2 ppm (20% mud), 0.1 ppm (10% mud), and water (0% mud). FIG. 10 is a graph showing fluorescence spectra measured using a laboratory spectrometer. FIG. 11 shows that intensity of fluorescence is almost proportional to dye concentration, and therefore WBM contaimination level. However, this relationship does not hold when the dye concentration is high. At high concentrations, saturation limits fluorescence intensity so sensitivity is reduced. For this reason, it is important to select an appropriate dye concentration to use. To avoid saturation effects, dye concentration must not be too high.

Figure 3:
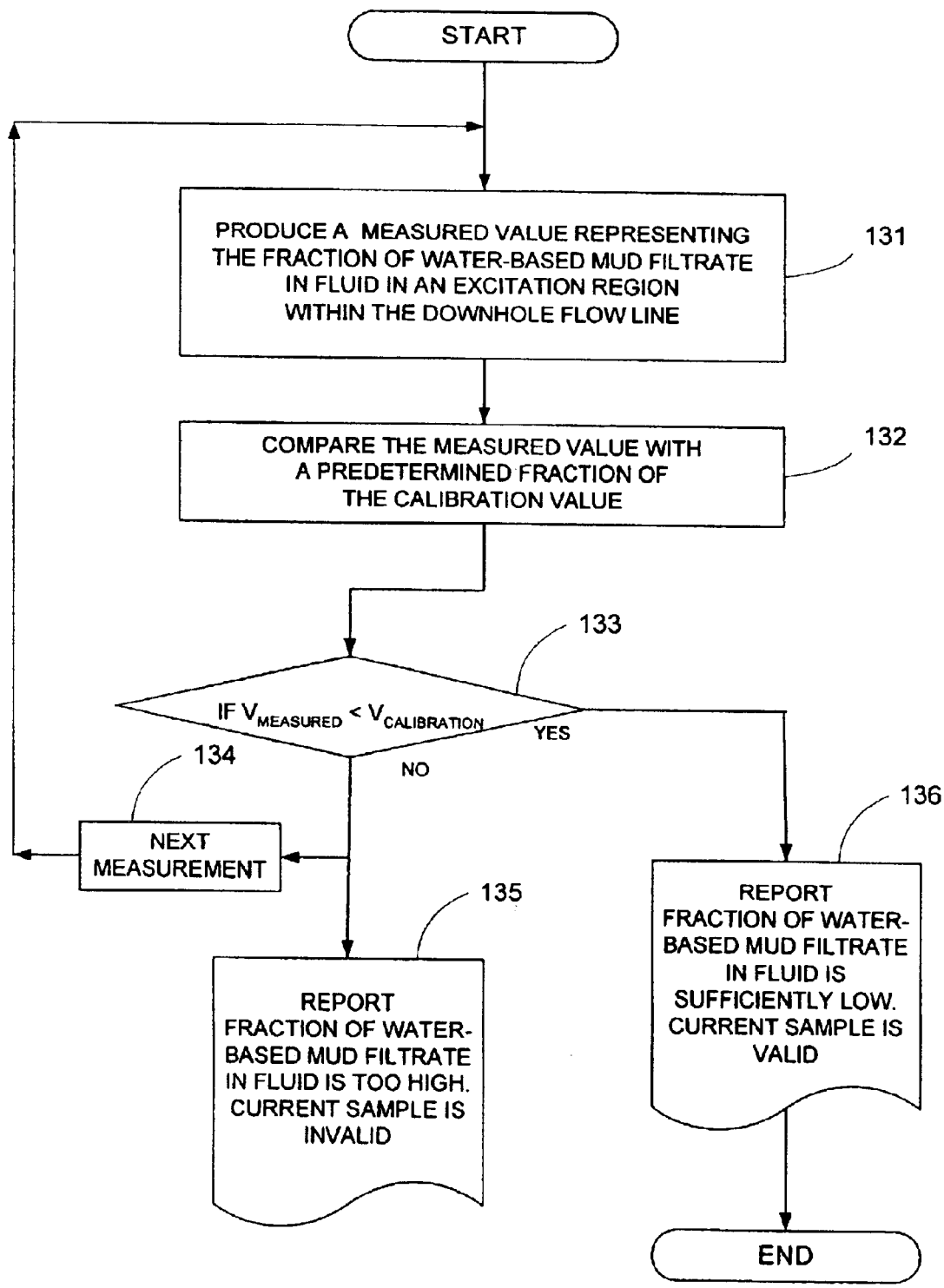
FIG. 3 is a flowchart of a method for validating downhole, in real time, a sample of connate water as having an acceptably low WBM filtrate contamination.

The invention also provides a method, illustrated in FIG. 3, for validating a sample of connate water as having an acceptably low WBM filtrate contamination. Each sample is drawn from formation at a selected depth and tested for validation downhole, in real time. Samples that are validated may be captured and brought to the surface for analysis. Samples that are not validated are typically discarded immediately. The method includes comparing measured fluorescence emission to a reference fluorescence emission. This method minimizes unnecessary time spent in flushing by capturing a sample as soon as the flushing process has produced a sample having an acceptably low WBM filtrate contamination.

Figure 4:
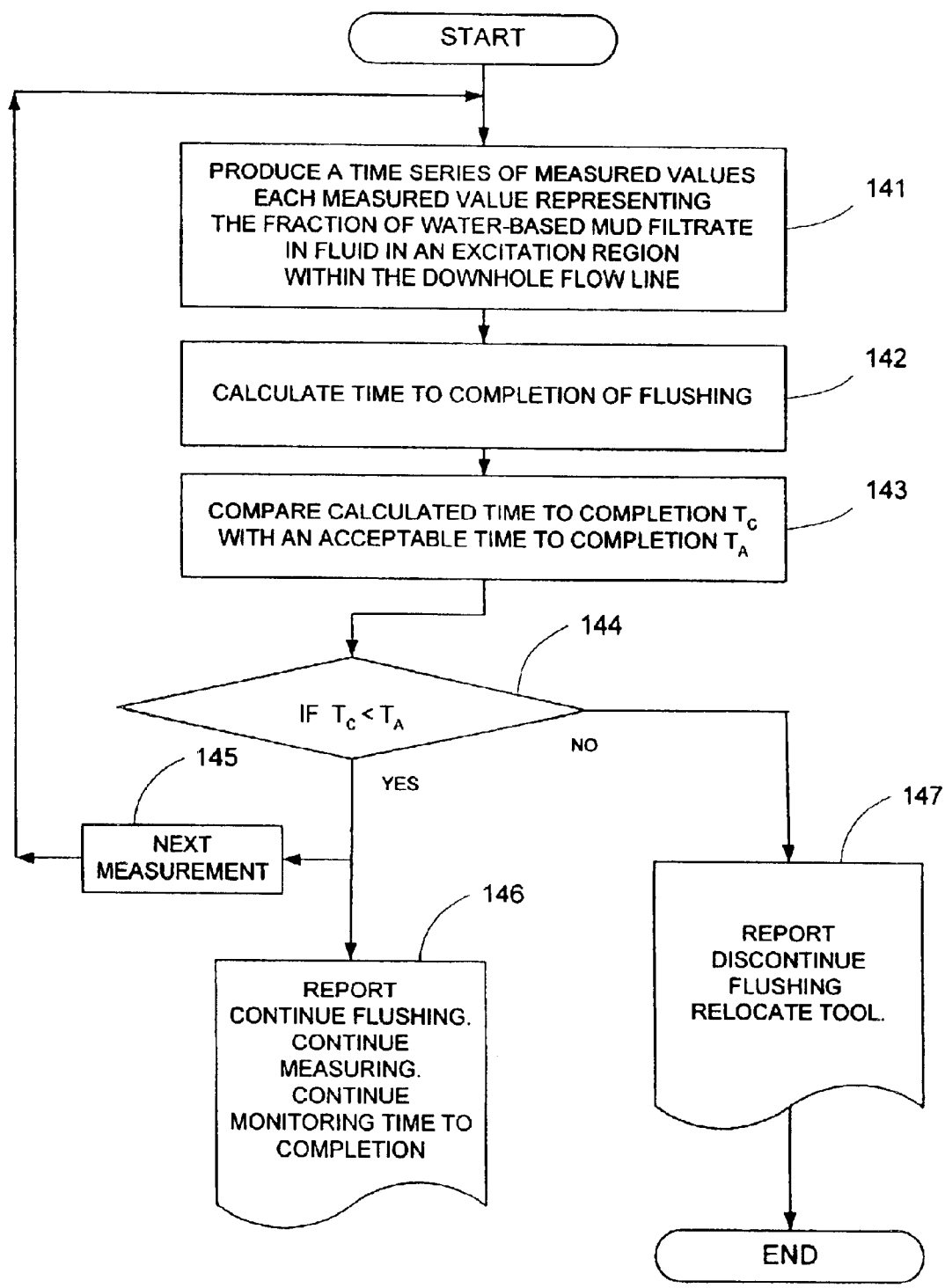
FIG. 4 is a flowchart of a method for predicting flushing time needed at a current vertical location of the tool to produce a sample having an acceptably low WBM filtrate contamination.
Figure 9:
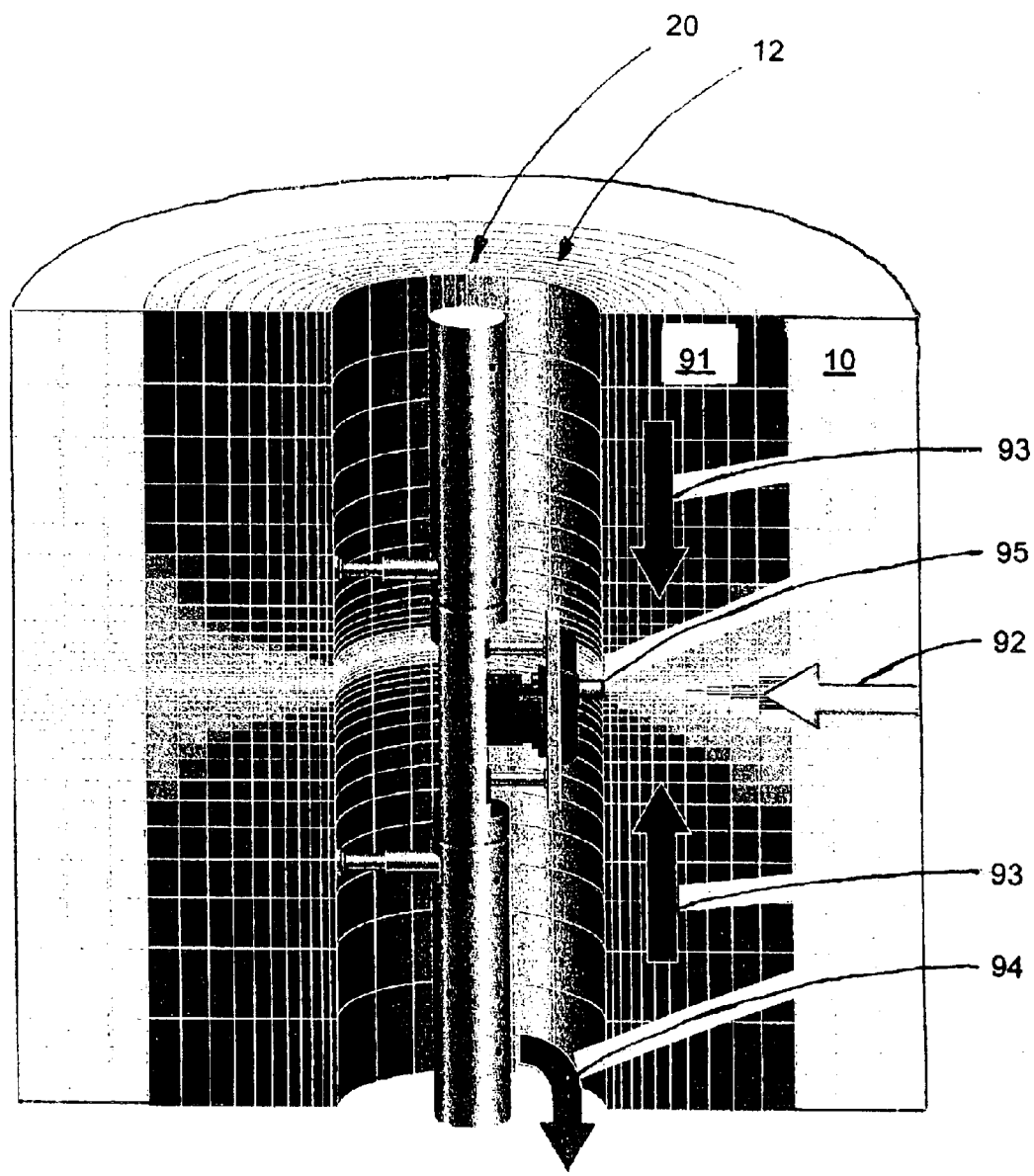
FIG. 9 shows an embodiment of a wireline tool according to the invention having a sample probe, in a schematic illustration of the spherical flow model used in analysis of the operation of the invention.

The invention also provides a method, illustrated in FIG. 4, for predicting flushing time needed at a current vertical location of the tool to produce a sample having an acceptably low WBM filtrate contamination. The process of flushing is illustrated in FIG. 9 with a probe embodiment. Formation fluid flow 92 (in this case connate water) is drawn towards the aperture of probe 95 and flushes away mud filtrate from a local region of the formation. FIG. 9 shows borehole surface region 91 as formation permeated by mud filtrate (in this case WBM with tracer dye. FIG. 9 shows borehole surface region 91 extending as a cylinder surrounding the borehole and the tool. "Flushing time to completion" is the time needed to produce a sample having an acceptably low WBM filtrate contamination. The method includes measuring fluorescence emission at successive times and monitoring rate of decrease of measured emission to produce a predicted flushing time. Knowledge of the predicted flushing time enables the tool operator to identify a location where flushing to produce a sample having an acceptably low WBM filtrate contamination would take an unreasonable time. On identifying such a location, the tool operator would typically abandon the current vertical location and move the tool to a next available vertical location.

Preferably, the tracer dye is Uranine (Fluorescein disodium salt). The dye is dissolved in water based mud (WBM) with a concentration of typically 1 ppm in weight. The concentration may be in the range from 0.1 ppm to 10 ppm. A concentration will be selected depending on the geometry and sensitivity of a particular fluorescence monitor.

Figure 5:
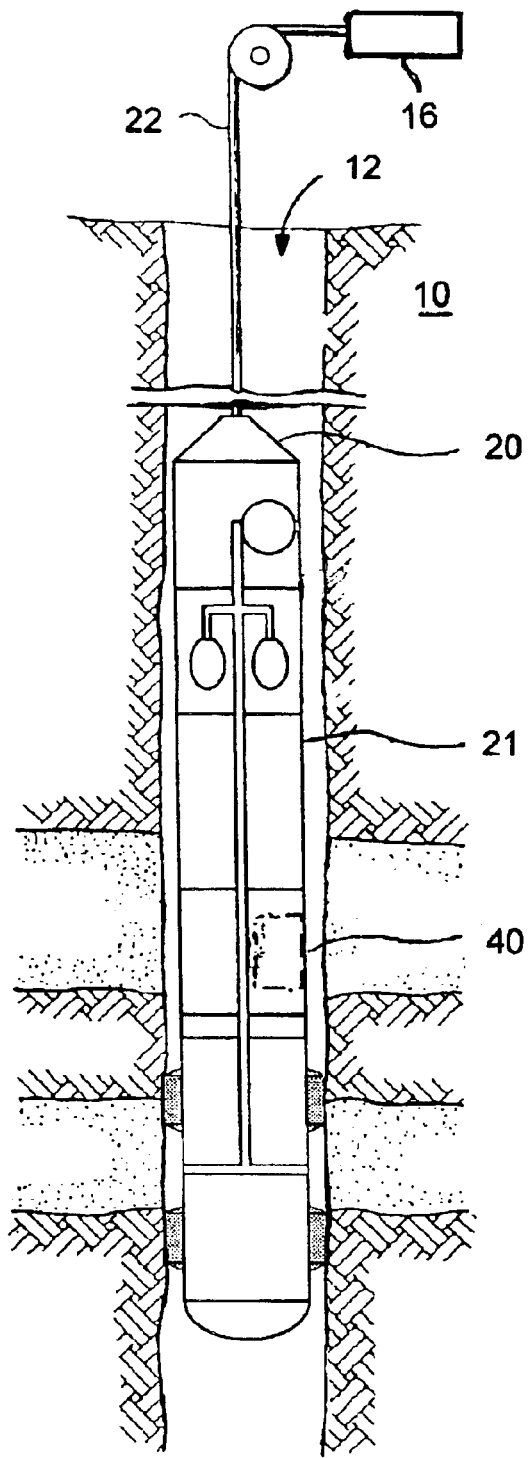
FIG. 5 is a schematic diagram of a wireline tool including a fluorescence monitor according to the invention.

FIG. 5 is a schematic diagram of a wireline operation including tool 20 and fluorescence monitor 40 according to the invention. Tool 20, having elongated body 21, is suspended in borehole 12 from the lower end of a logging cable 22 that is connected in a conventional fashion to a surface system 16 incorporating appropriate electronics and processing systems for control of the tool. Fluorescence monitor 40 is included within tool body 21.

Figure 6:
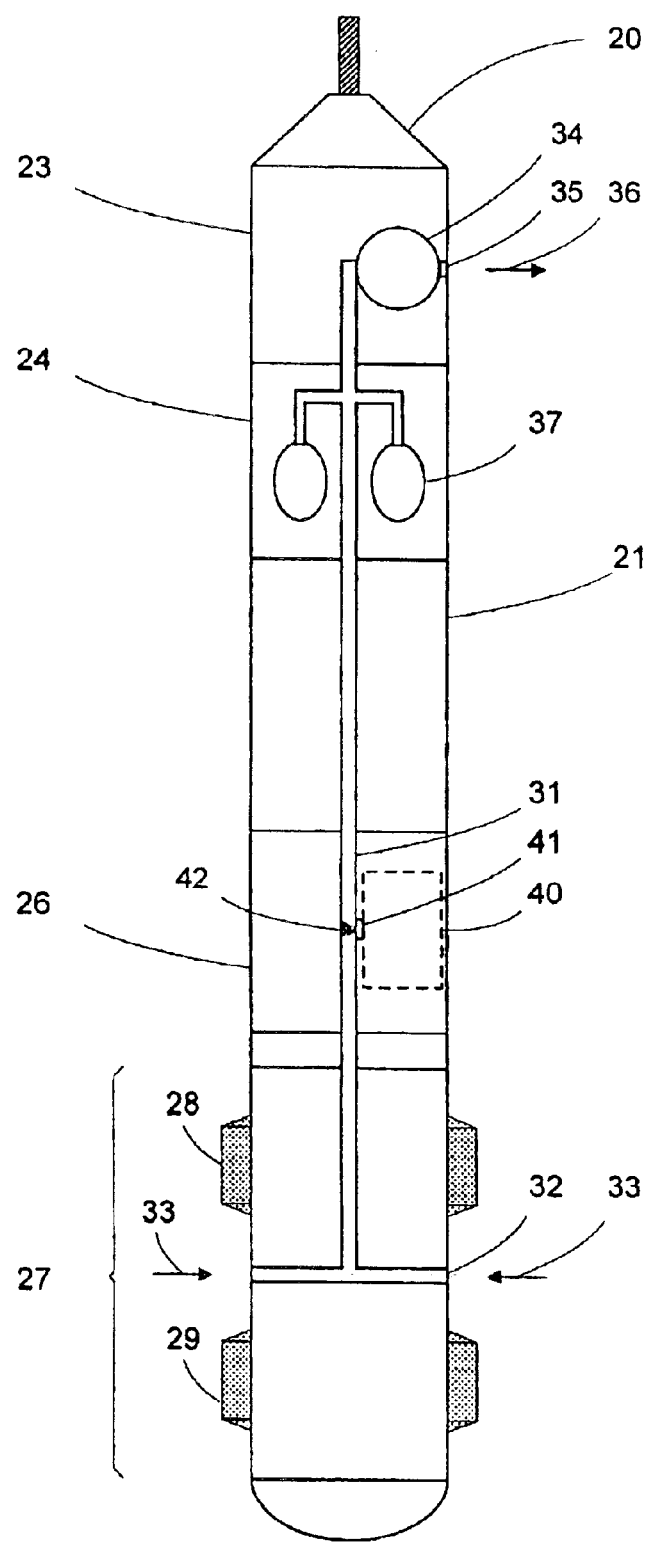
FIG. 6 is a schematic diagram locating several modules of the wireline tool of FIG. 5, and showing the fluorescence monitor in the fluid analysis module.
Figure 8:
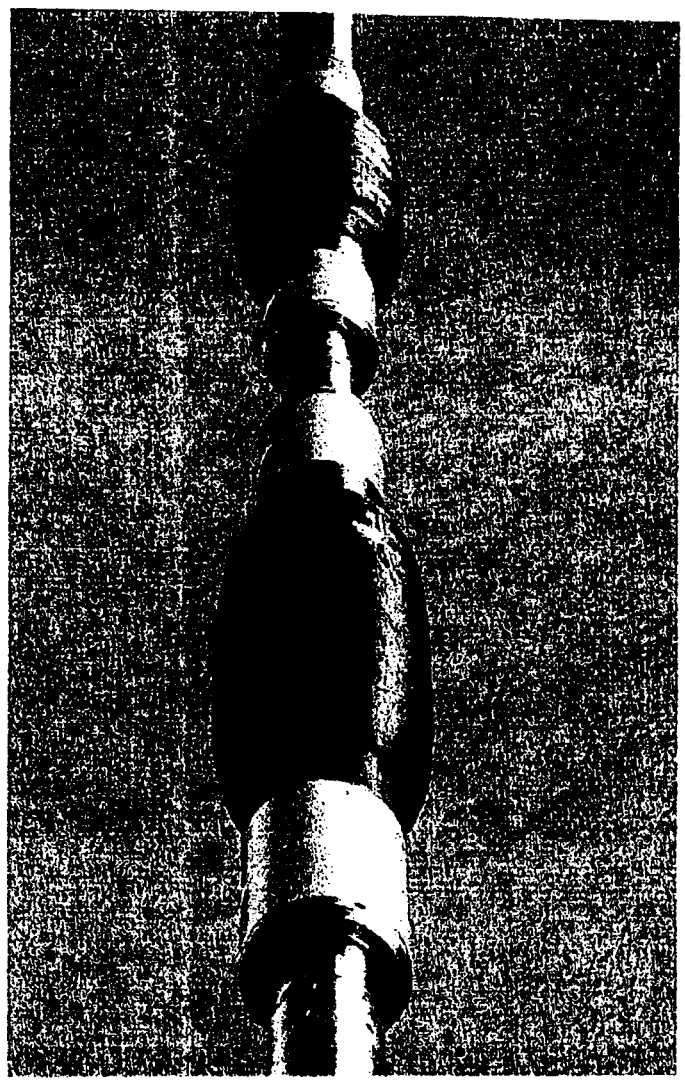
FIG. 8 is an image of a dual packer module used in the first preferred embodiment of a tool according to the invention.

FIG. 6 is a schematic diagram of wireline tool 20. Elongated body 21 includes pump out module 23, sample chambers module 24, fluorescence module 26, and dual packer module 27. (Other prior art modules, including power cartridge, hydraulic module, and flow control module that are normally present are not shown in FIG. 6). Fluorescence module 26 contains fluorescence monitor 40. Dual packer module 27 is equipped for selectively sealing off or isolating portions of the wall of the borehole between upper packer 28 and lower packer 29, such that pressure or fluid communication with the adjacent earth formation is established. FIG. 8 is an image of dual packer module 27.

Elongated body 21 defines flow line 31 and fluid admitting aperture 32. Formation fluid inflow is indicated by arrow 33. Elongated body 21 also includes piston pump 34 and defines fluid exit aperture 35. Formation fluid outflow back into the borehole is indicated by arrow 36. Piston pump 34 provides the pressure to drive fluid sample through the flow line and though the sample cell. Tool 20 also includes sample chambers 37 for capturing and carrying fluid samples to the surface for analysis.

A description of a wireline tool such as shown in FIG. 6, but without the fluorescence monitor of the present invention, is found in U.S. Pat. No. 4,860,581, issued Aug. 29, 1989, to Zimmerman et al. A copy of U.S. Pat. No. 4,860,581 is hereby incorporated herein by reference.

Figure 7:
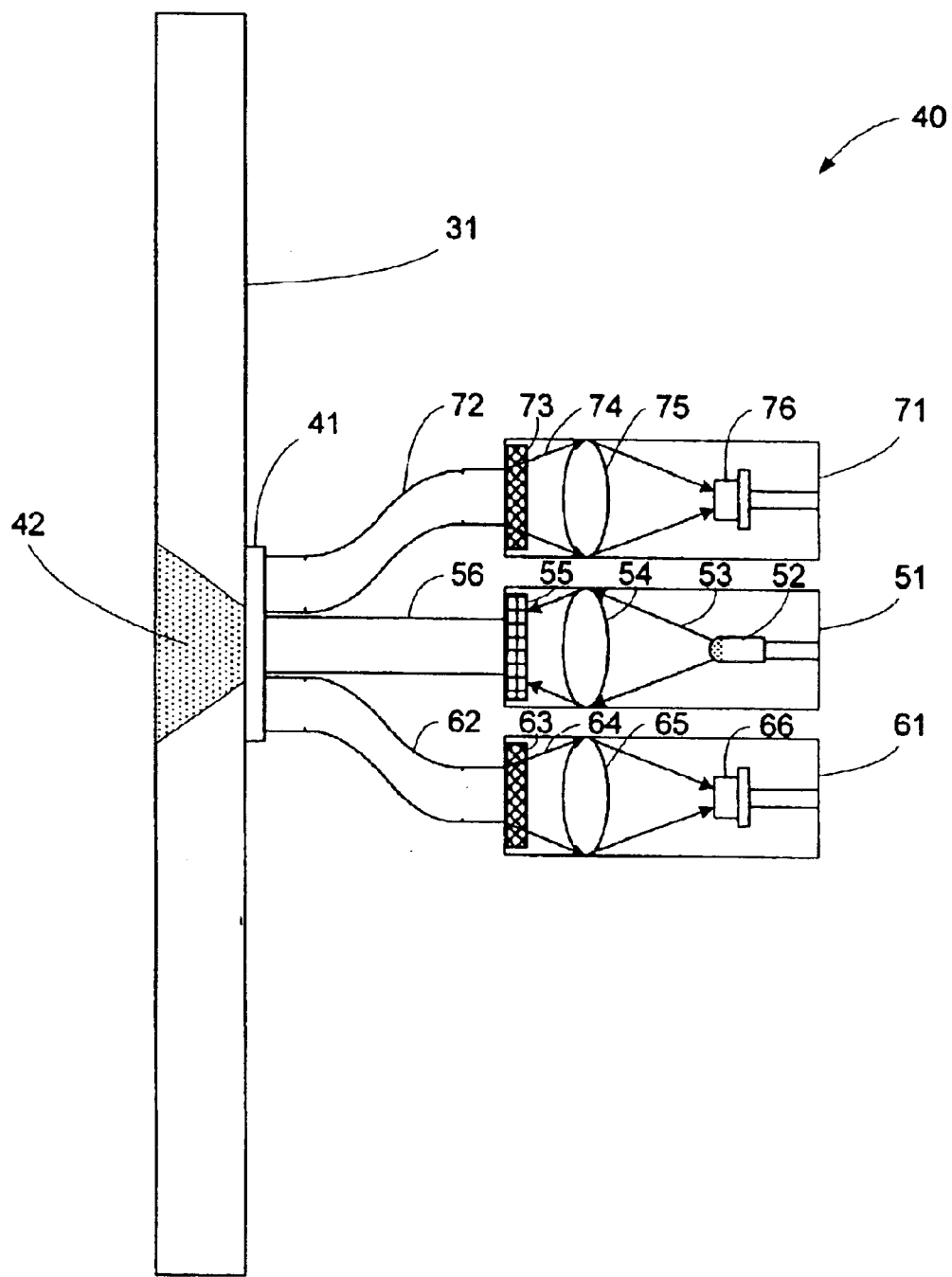
FIG. 7 is a schematic illustration of a first preferred embodiment of a fluorescence monitor according to the invention.

FIG. 7 shows detail of preferred optics of fluorescence monitor 40. The preferred embodiment includes a portion of flow line 31 having a sapphire optical window 41. Flow line 31 and excitation light source 51 define fluid sample excitation region 42. Fluorescence monitor 40 includes the sapphire optical window 41, excitation light source (490 nm) 51, first fluorescence detector (540 nm) 61, second fluorescence detector (600 nm) 71. Excitation light source 51 includes light-emitting diode (LED) 52 (shown emitting fluorescence excitation, 490 nm, light rays 53), converging lens 54, short-pass optical filter (<490 nm), and glass rod light pipe 56. First fluorescence detector (540 nm) 61 includes glass conduit light pipe 62 and long-pass optical filter (>540 nm) 63 (shown passing fluorescence emission rays (540 nm) 64), converging lens 65, and first fluorescence sensor (540 nm) 66. Second fluorescence detector (600 nm) 71 includes glass conduit light pipe 72 and long-pass optical filter (>600 nm) 73 (shown passing fluorescence emission rays (600 nm) 74), converging lens 75, and first fluorescence sensor (600 nm) 76. Fluorescence monitor 40 also includes data base means, and a processing means (not shown).

Fluids drawn from the formation into fluid sample excitation region 42 are illuminated by excitation light. Emitted fluorescent light is detected to produce fluorescence intensity and other signals. The signals are processed, based on information in the data base relating to the different types of light, to measure fluorescence emission and to determine sample validity or to predict flushing time. The excitation wavelength is preferably 490 nm. The fluorescence detection wavelengths are preferably 540 nm and 600 nm. Pressure to draw the sample is provided by a piston pump 34 of FIG. 6. Measurements are made of fluorescence from a flowing sample in an excitation region 42 of flow line 31, as shown in FIG. 7.

FIG. 9 shows a schematic illustration of the spherical flow model used in analysis of the operation of the invention. The wireline tool shown in FIG. 9 includes a sample probe 95. This is an alternative to the preferred dual packer embodiment.

We claim:

1. A method for assessing water-based mud filtrate concentration in a downhole fluid sample drawn from the borehole of an oil well, comprising:

a) pumping a water-based mud having a water-soluble fluorescent dye tracer into the borehole;

b) pumping sample fluid from a selected downhole location through a downhole flow line;

c) illuminating sample fluid in an excitation region of the downhole flow line with fluorescence excitation light; and d) measuring fluorescence emission from the excitation region to produce a measured value representing the fraction of water-based mud filtrate in the sample fluid.

2. A method according to claim 1, further comprising:

e) establishing a calibration value representing 100% water-based mud filtrate.

3. A method according to claim 2, wherein the calibration value is established by pumping substantially 100% water-based mud filtrate through the downhole flow line and measuring fluorescence emission from the excitation region.

4. A method according to claim 2, wherein the calibration value is established by measuring fluorescence emission in a laboratory.

5. A method according to claim 2, further comprising:

f) repeating b), c), and d) to produce a series of measured values representing the fraction of water-based mud filtrate in each of a series of downhole fluid samples;

g) comparing each measured value of the series of measured values with a predetermined fraction of the calibration value; and h) validating a downhole fluid sample as having an acceptably low fraction of water-based mud filtrate when the measured value of the sample is less than the predetermined fraction of the calibration value.

6. A method according to claim 2, further comprising:

i) repeating b), c), and d) at intervals of time to produce time series data including a series of times, and a corresponding series of measured values representing the fraction of water-based mud filtrate in each of a series of downhole fluid samples; and j) using the time series data and a predetermined fraction of the calibration value to calculate a predicted flushing time to completion.

7. A method according to claim 6, further comprising:

k) comparing calculated flushing time to completion with a predetermined acceptable time to completion.

8. A tool for assessing water-based mud filtrate concentration in a downhole fluid sample drawn from the borehole of an oil well containing water-based mud with a water-soluble fluorescent dye tracer, comprising:

an elongated body containing a flow line having a window, the flow line containing an excitation region proximate to the window;

a pump configured to pump sample fluid from a selected downhole location through the flow line;

means for illuminating sample fluid in the excitation region with fluorescence excitation light; and means for measuring fluorescence emission from the excitation region and producing a measured value representing the fraction of water-based mud filtrate in the sample fluid.

9. A tool according to claim 8, further comprising:

means for establishing a calibration value representing 100% water-based mud filtrate.

10. A tool according to claim 8, further comprising:

means for producing a series of measured values representing the fraction of water-based mud filtrate in each of a series of downhole fluid samples;

means for comparing each measured value of the series of measured values with a predetermined fraction of a calibration value; and means for validating a downhole fluid sample as having an acceptably low fraction of water-based mud filtrate when the measured value of the sample is less than the predetermined fraction of the calibration value.

11. A tool according to claim 8, further comprising:

means for producing a series of measured values at intervals of time to produce time series data including a series of times, and a corresponding series of measured values representing the fraction of water-based mud filtrate in each of a series of downhole fluid samples; and means for using the time series data and a predetermined fraction of a calibration value to calculate a predicted flushing time to completion.

* * * * *